(12) United States Patent
Buan et al.

(10) Patent No.: US 10,111,991 B2
(45) Date of Patent: *Oct. 30, 2018

(54) NEGATIVE PRESSURE WOUND THERAPY DEVICE

(71) Applicant: Smith & Nephew, Inc., Memphis, TN (US)

(72) Inventors: John Buan, Maple Grove, MN (US); Alan Carson, St. Paul, MN (US); Daniel Gelfman, Golden Valley, MN (US)

(73) Assignee: Smith & Nephew, Inc., Memphis, TN (US)

( * ) Notice: Subject to any disclaimer, the term of this patent is extended or adjusted under 35 U.S.C. 154(b) by 13 days.

This patent is subject to a terminal disclaimer.

(21) Appl. No.: 15/278,811

(22) Filed: Sep. 28, 2016

(65) Prior Publication Data

US 2017/0014276 A1 Jan. 19, 2017

Related U.S. Application Data

(63) Continuation of application No. 14/179,893, filed on Feb. 13, 2014, now Pat. No. 9,579,431, which is a
(Continued)

(51) Int. Cl.
*A61M 1/00* (2006.01)
*A61F 13/00* (2006.01)
(Continued)

(52) U.S. Cl.
CPC ..... *A61M 1/0088* (2013.01); *A61F 13/00068* (2013.01); *A61F 13/0206* (2013.01);
(Continued)

(58) Field of Classification Search
CPC ......... A61M 1/00; A61M 27/00; A61F 13/00; A61F 13/02; A61K 9/22
See application file for complete search history.

(56) References Cited

U.S. PATENT DOCUMENTS

| 59,388 A | 11/1866 | Hadfield |
| 695,270 A | 3/1902 | Beringer |

(Continued)

FOREIGN PATENT DOCUMENTS

| CA | 2 198 243 | 2/1996 |
| CA | 2 367 460 | 10/2000 |

(Continued)

OTHER PUBLICATIONS

US 6,306,115, 10/2001, Kelly et al. (withdrawn)
(Continued)

*Primary Examiner* — Tatyana Zalukaeva
*Assistant Examiner* — Ilya Treyger
(74) *Attorney, Agent, or Firm* — Knobbe, Martens, Olson & Bear, LLP

(57) ABSTRACT

A wound therapy device and a kit for same with a housing material, a gasket disposed around at least a portion of the housing material, a non-woven absorption material, and a port. The gasket is sized and configured such that at least a first portion of the gasket will be adhered to a second portion of the gasket upon a folding of the housing material. A method of using a wound therapy device.

10 Claims, 2 Drawing Sheets

Related U.S. Application Data continuation of application No. 12/762,149, filed on Apr. 16, 2010, now Pat. No. 8,663,198.

(60) Provisional application No. 61/212,947, filed on Apr. 17, 2009.

(51) Int. Cl.
*A61F 13/02* (2006.01)
*A61F 17/00* (2006.01)
*A61F 13/06* (2006.01)
*A61F 13/514* (2006.01)
*A61M 27/00* (2006.01)
*A61K 9/22* (2006.01)

(52) U.S. Cl.
CPC ...... *A61F 13/0216* (2013.01); *A61F 13/0253* (2013.01); *A61F 13/0259* (2013.01); *A61F 13/064* (2013.01); *A61F 13/51456* (2013.01); *A61F 17/00* (2013.01); *A61M 2210/086* (2013.01)

(56) References Cited

U.S. PATENT DOCUMENTS

| | | | |
|---|---|---|---|
| 1,480,562 | A | 1/1924 | Mock |
| 1,629,108 | A | 5/1927 | Lake |
| 2,280,915 | A | 4/1942 | Johnson |
| 2,367,690 | A | 7/1943 | Purdy |
| 2,568,933 | A | 9/1951 | Robbins |
| 2,632,443 | A | 3/1953 | Lesher |
| 2,682,873 | A | 7/1954 | Evans et al. |
| 3,367,332 | A | 2/1968 | Groves |
| 3,486,504 | A | 12/1969 | Austin, Jr. |
| 3,495,590 | A | 2/1970 | Zeiller |
| 3,572,340 | A | 3/1971 | Lloyd et al. |
| 3,610,238 | A | 10/1971 | Rich, Jr. |
| 3,727,629 | A | 4/1973 | Gifford |
| 3,874,387 | A | 4/1975 | Barbieri |
| 3,972,328 | A | 8/1976 | Chen |
| 3,993,080 | A | 11/1976 | Loseff |
| RE29,319 | E | 7/1977 | Nordby et al. |
| 4,102,342 | A | 7/1978 | Akiyama et al. |
| 4,112,947 | A | 9/1978 | Nehring |
| 4,136,696 | A | 1/1979 | Nehring |
| 4,139,004 | A | 2/1979 | Gonzalez, Jr. |
| 4,184,510 | A | 1/1980 | Murry et al. |
| 4,217,894 | A | 8/1980 | Franetzki |
| 4,219,019 | A | 8/1980 | Coates |
| 4,224,945 | A | 9/1980 | Cohen |
| 4,250,882 | A | 2/1981 | Adair |
| 4,316,466 | A | 2/1982 | Babb |
| 4,353,359 | A | 10/1982 | Milbauer |
| 4,382,441 | A | 5/1983 | Svedman |
| 4,396,023 | A | 8/1983 | Anderson |
| 4,465,485 | A | 8/1984 | Kashmer et al. |
| 4,468,227 | A | 8/1984 | Jensen |
| 4,523,920 | A | 6/1985 | Russo |
| 4,525,166 | A | 6/1985 | Leclerc |
| 4,533,352 | A | 8/1985 | Van Beek et al. |
| 4,534,356 | A | 8/1985 | Papadakis |
| 4,551,141 | A | 11/1985 | McNeil |
| 4,573,965 | A | 3/1986 | Russo |
| 4,608,041 | A | 8/1986 | Nielsen |
| 4,621,624 | A | 11/1986 | Rayboy |
| 4,655,766 | A | 4/1987 | Theeuwes et al. |
| 4,681,562 | A | 7/1987 | Beck et al. |
| 4,710,165 | A | 12/1987 | McNeil et al. |
| 4,768,501 | A | 9/1988 | George |
| 4,772,259 | A | 9/1988 | Frech et al. |
| 4,778,446 | A | 10/1988 | Jensen |
| 4,778,456 | A | 10/1988 | Lokken |
| 4,790,833 | A | 12/1988 | Schmidt |
| 4,792,328 | A | 12/1988 | Beck et al. |
| 4,795,435 | A | 1/1989 | Steer |
| 4,817,590 | A | 4/1989 | Stancik, Jr. |
| 4,820,284 | A | 4/1989 | Hauri |
| 4,828,546 | A | 5/1989 | McNeil et al. |
| 4,921,488 | A | 5/1990 | Maitz et al. |
| 4,936,834 | A | 6/1990 | Beck et al. |
| 4,950,483 | A | 8/1990 | Ksander et al. |
| 4,969,880 | A | 11/1990 | Zamierowski |
| 4,972,829 | A | 11/1990 | Knerr |
| 4,979,944 | A | 12/1990 | Luzsicza |
| 4,994,022 | A | 2/1991 | Steffler et al. |
| 5,055,198 | A | 10/1991 | Shettigar |
| 5,056,510 | A | 10/1991 | Gilman |
| 5,073,172 | A | 12/1991 | Fell |
| 5,100,396 | A | 3/1992 | Zamierowski |
| 5,149,331 | A | 9/1992 | Ferdman et al. |
| 5,152,757 | A | 10/1992 | Eriksson |
| 5,167,613 | A | 12/1992 | Karami et al. |
| 5,176,663 | A | 1/1993 | Svedman et al. |
| 5,215,519 | A | 6/1993 | Shettigar |
| 5,238,732 | A | 8/1993 | Krishnan |
| 5,261,893 | A | 11/1993 | Zamierowski |
| 5,266,928 | A | 11/1993 | Johnson |
| 5,279,608 | A | 1/1994 | Cherif Cheikh |
| 5,328,614 | A | 7/1994 | Matsumura |
| 5,358,494 | A | 10/1994 | Svedman |
| 5,380,280 | A | 1/1995 | Peterson |
| 5,437,651 | A | 8/1995 | Todd et al. |
| 5,445,604 | A | 8/1995 | Lang |
| 5,489,280 | A | 2/1996 | Russell |
| 5,498,338 | A | 3/1996 | Kruger et al. |
| 5,514,166 | A | 5/1996 | Silver et al. |
| 5,527,293 | A | 6/1996 | Zamierowski |
| 5,549,584 | A | 8/1996 | Gross |
| 5,562,107 | A | 10/1996 | Lavender et al. |
| 5,636,643 | A | 6/1997 | Argenta et al. |
| 5,643,189 | A | 7/1997 | Masini |
| 5,645,081 | A | 7/1997 | Argenta et al. |
| 5,678,564 | A | 10/1997 | Lawrence et al. |
| 5,688,225 | A | 11/1997 | Walker |
| 5,733,337 | A | 3/1998 | Carr et al. |
| 5,759,570 | A | 6/1998 | Arnold |
| 5,785,688 | A | 7/1998 | Joshi et al. |
| 5,830,496 | A | 11/1998 | Freeman |
| 5,833,646 | A | 11/1998 | Masini |
| 5,843,011 | A | 12/1998 | Lucas |
| 5,848,998 | A | 12/1998 | Marasco, Jr. |
| 5,857,502 | A | 1/1999 | Buchalter |
| 5,865,772 | A | 2/1999 | George |
| 5,868,933 | A | 2/1999 | Patrick et al. |
| 5,876,611 | A | 3/1999 | Shettigar |
| 5,964,723 | A | 10/1999 | Augustine |
| 5,970,542 | A * | 10/1999 | Mays ............ A47G 9/066 2/69.5 |
| 6,063,980 | A | 5/2000 | Peterson et al. |
| 6,071,267 | A | 6/2000 | Zamierowski |
| 6,103,951 | A | 8/2000 | Freeman |
| 6,110,197 | A | 8/2000 | Augustine et al. |
| 6,135,116 | A | 10/2000 | Vogel et al. |
| D434,150 | S | 11/2000 | Turney et al. |
| 6,142,982 | A | 11/2000 | Hunt et al. |
| 6,168,800 | B1 | 1/2001 | Dobos et al. |
| 6,176,307 | B1 | 1/2001 | Danos et al. |
| 6,225,523 | B1 | 5/2001 | Masini |
| 6,254,567 | B1 | 7/2001 | Treu et al. |
| 6,255,552 | B1 | 7/2001 | Cummings et al. |
| 6,261,283 | B1 | 7/2001 | Morgan et al. |
| 6,287,521 | B1 | 9/2001 | Quay et al. |
| 6,345,623 | B1 | 2/2002 | Heaton et al. |
| 6,398,767 | B1 | 6/2002 | Fleischmann |
| 6,402,724 | B1 | 6/2002 | Smith et al. |
| 6,440,167 | B2 | 8/2002 | Shimizu |
| 6,450,773 | B1 | 9/2002 | Upton |
| 6,458,109 | B1 | 10/2002 | Henley et al. |
| 6,465,708 | B1 | 10/2002 | Augustine |
| 6,471,685 | B1 | 10/2002 | Johnson |
| 6,471,982 | B1 | 10/2002 | Lydon et al. |
| 6,482,491 | B1 | 11/2002 | Samuelsen et al. |
| 6,491,684 | B1 | 12/2002 | Joshi et al. |
| 6,547,756 | B1 | 4/2003 | Greter et al. |

(56) References Cited

U.S. PATENT DOCUMENTS

| | | |
|---|---|---|
| 6,553,998 B2 | 4/2003 | Heaton et al. |
| 6,599,262 B1 | 7/2003 | Masini |
| 6,626,891 B2 | 9/2003 | Ohmstede |
| 6,648,862 B2 | 11/2003 | Watson |
| 6,673,028 B1 | 1/2004 | Argenta et al. |
| 6,676,610 B2 | 1/2004 | Morton et al. |
| 6,685,681 B2 | 2/2004 | Lockwood et al. |
| 6,695,823 B1 | 2/2004 | Lina et al. |
| 6,695,824 B2 | 2/2004 | Howard et al. |
| 6,752,794 B2 | 6/2004 | Lockwood et al. |
| 6,755,807 B2 | 6/2004 | Risk et al. |
| 6,764,462 B2 | 7/2004 | Risk, Jr. et al. |
| 6,767,334 B1 | 7/2004 | Randolph |
| 6,787,682 B2 | 9/2004 | Gilman |
| 6,814,079 B2 | 11/2004 | Heaton et al. |
| 6,824,533 B2 | 11/2004 | Risk, Jr. et al. |
| 6,855,135 B2 | 2/2005 | Lockwood et al. |
| 6,856,821 B2 | 2/2005 | Johnson |
| 6,936,037 B2 | 8/2005 | Bubb |
| 6,951,553 B2 | 10/2005 | Bubb et al. |
| 6,960,179 B2 | 11/2005 | Gura |
| 6,977,323 B1 | 12/2005 | Swenson |
| 6,979,324 B2 | 12/2005 | Bybordi et al. |
| 6,994,702 B1 | 2/2006 | Johnson |
| 7,004,915 B2 | 2/2006 | Boynton et al. |
| 7,022,113 B2 | 4/2006 | Lockwood et al. |
| 7,067,709 B2 | 6/2006 | Murate et al. |
| 7,070,584 B2 | 7/2006 | Johnson et al. |
| 7,077,832 B2 | 7/2006 | Fleischmann |
| 7,087,806 B2 | 8/2006 | Scheinberg et al. |
| 7,108,683 B2 | 9/2006 | Zamierowski |
| 7,117,869 B2 | 10/2006 | Heaton et al. |
| 7,118,545 B2 | 10/2006 | Boyde |
| 7,128,735 B2 | 10/2006 | Weston |
| 7,141,714 B2 | 11/2006 | Nielsen |
| 7,195,624 B2 | 3/2007 | Lockwood |
| 7,214,202 B1 | 5/2007 | Vogel et al. |
| 7,216,651 B2 | 5/2007 | Argenta et al. |
| 7,235,066 B1 | 6/2007 | Narini et al. |
| 7,279,612 B1 | 10/2007 | Heaton et al. |
| 7,361,184 B2 | 4/2008 | Joshi |
| 7,381,859 B2 | 6/2008 | Hunt et al. |
| 7,438,705 B2 | 10/2008 | Karpowicz et al. |
| 7,470,830 B2 | 12/2008 | Sigurjonsson et al. |
| 7,494,482 B2 | 2/2009 | Orgill et al. |
| 7,507,870 B2 | 3/2009 | Nielsen et al. |
| 7,524,286 B2 | 4/2009 | Johnson |
| 7,524,315 B2 | 4/2009 | Blott et al. |
| 7,534,240 B1 | 5/2009 | Johnson |
| 7,534,927 B2 | 5/2009 | Lockwood |
| 7,553,306 B1 | 6/2009 | Hunt et al. |
| 7,569,742 B2 | 8/2009 | Haggstrom et al. |
| 7,611,500 B1 | 11/2009 | Lina et al. |
| 7,612,247 B2 | 11/2009 | Oyaski |
| 7,615,036 B2 | 11/2009 | Joshi et al. |
| 7,625,362 B2 | 12/2009 | Boehringer et al. |
| 7,645,253 B2 | 1/2010 | Gura et al. |
| 7,645,269 B2 | 1/2010 | Zamierowski |
| 7,699,823 B2 | 4/2010 | Haggstrom et al. |
| 7,699,830 B2 | 4/2010 | Martin |
| 7,700,819 B2 | 4/2010 | Ambrosio et al. |
| 7,708,724 B2 | 5/2010 | Weston |
| 7,717,313 B2 | 5/2010 | Criscuolo et al. |
| 7,731,702 B2 | 6/2010 | Bybordi et al. |
| 7,753,894 B2 | 7/2010 | Blott et al. |
| 7,759,537 B2 | 7/2010 | Bishop et al. |
| 7,759,538 B2 | 7/2010 | Fleischmann |
| 7,759,539 B2 | 7/2010 | Shaw et al. |
| 7,775,998 B2 | 8/2010 | Riesinger |
| 7,776,028 B2 | 8/2010 | Miller et al. |
| 7,779,625 B2 | 8/2010 | Joshi et al. |
| 7,790,945 B1 | 9/2010 | Watson, Jr. |
| 7,790,946 B2 | 9/2010 | Mulligan |
| 7,794,438 B2 | 9/2010 | Henley et al. |
| 7,794,450 B2 | 9/2010 | Blott et al. |
| 7,811,269 B2 | 10/2010 | Boynton et al. |
| 7,815,616 B2 | 10/2010 | Boehringer et al. |
| 7,825,289 B2 | 11/2010 | Vess |
| 7,828,782 B2 | 11/2010 | Suzuki |
| 7,838,717 B2 | 11/2010 | Haggstrom et al. |
| 7,846,141 B2 | 12/2010 | Weston |
| 7,858,838 B2 | 12/2010 | Holm et al. |
| 7,862,339 B2 | 1/2011 | Mulligan |
| 7,883,494 B2 | 2/2011 | Martin |
| 7,896,856 B2 | 3/2011 | Petrosenko et al. |
| 7,909,805 B2 | 3/2011 | Weston |
| 7,910,791 B2 | 3/2011 | Coffey |
| 7,922,703 B2 | 4/2011 | Riesinger |
| 7,927,318 B2 | 4/2011 | Risk, Jr. et al. |
| 7,931,630 B2 | 4/2011 | Nishtala et al. |
| 7,959,624 B2 | 6/2011 | Riesinger |
| 7,964,766 B2 | 6/2011 | Blott et al. |
| 7,976,519 B2 | 7/2011 | Bubb et al. |
| 7,998,125 B2 | 8/2011 | Weston |
| 8,012,169 B2 | 9/2011 | Joshi |
| 8,034,037 B2 | 10/2011 | Adams et al. |
| 8,062,272 B2 | 11/2011 | Weston |
| 8,062,273 B2 | 11/2011 | Weston |
| 8,080,702 B2 | 12/2011 | Blott et al. |
| 8,084,663 B2 | 12/2011 | Watson, Jr. |
| 8,100,887 B2 | 1/2012 | Weston et al. |
| 8,105,295 B2 | 1/2012 | Blott et al. |
| 8,118,794 B2 | 2/2012 | Weston et al. |
| 8,128,615 B2 | 3/2012 | Blott et al. |
| 8,133,211 B2 | 3/2012 | Cavanaugh, II et al. |
| 8,147,468 B2 | 4/2012 | Barta et al. |
| 8,152,785 B2 | 4/2012 | Vitaris |
| 8,162,907 B2 | 4/2012 | Heagle |
| 8,162,909 B2 | 4/2012 | Blott et al. |
| 8,188,331 B2 | 5/2012 | Barta et al. |
| 8,202,261 B2 | 6/2012 | Kazala, Jr. et al. |
| 8,207,392 B2 | 6/2012 | Haggstrom et al. |
| 8,235,955 B2 | 8/2012 | Blott et al. |
| 8,241,261 B2 | 8/2012 | Randolph et al. |
| 8,251,979 B2 | 8/2012 | Malhi |
| 8,257,326 B2 | 9/2012 | Vitaris |
| 8,257,327 B2 | 9/2012 | Blott et al. |
| 8,257,328 B2 | 9/2012 | Augustine et al. |
| 8,282,611 B2 | 10/2012 | Weston |
| 8,294,586 B2 | 10/2012 | Pidgeon et al. |
| 8,298,200 B2 | 10/2012 | Vess et al. |
| 8,303,552 B2 | 11/2012 | Weston |
| 8,308,714 B2 | 11/2012 | Weston et al. |
| 8,323,264 B2 | 12/2012 | Weston et al. |
| 8,348,910 B2 | 1/2013 | Blott et al. |
| 8,398,614 B2 | 3/2013 | Blott et al. |
| 8,404,921 B2 | 3/2013 | Lee et al. |
| 8,444,612 B2 | 5/2013 | Patel et al. |
| 8,449,509 B2 | 5/2013 | Weston |
| 8,494,349 B2 | 7/2013 | Gordon |
| 8,535,296 B2 | 9/2013 | Blott et al. |
| 8,569,566 B2 | 10/2013 | Blott et al. |
| 8,641,691 B2 | 2/2014 | Fink |
| 8,663,198 B2 | 3/2014 | Buan et al. |
| 8,708,998 B2 | 4/2014 | Weston et al. |
| 8,715,256 B2 | 5/2014 | Greener |
| 8,764,732 B2 | 7/2014 | Hartwell |
| 8,808,274 B2 | 8/2014 | Hartwell |
| 8,814,842 B2 | 8/2014 | Coulthard et al. |
| 8,905,985 B2 | 12/2014 | Hull et al. |
| 8,926,592 B2 | 1/2015 | Blott et al. |
| 9,011,353 B2 | 4/2015 | Hardman et al. |
| 9,044,579 B2 | 6/2015 | Blott et al. |
| 9,061,095 B2 | 6/2015 | Adie et al. |
| 9,084,845 B2 | 7/2015 | Adie et al. |
| 9,579,431 B2 | 2/2017 | Buan et al. |
| 2001/0016205 A1 | 8/2001 | Shimizu |
| 2001/0016781 A1 | 8/2001 | Caspers |
| 2001/0029956 A1 | 10/2001 | Argenta |
| 2001/0034499 A1 | 10/2001 | Sessions et al. |
| 2002/0065494 A1 | 5/2002 | Lockwood et al. |
| 2002/0068913 A1 | 6/2002 | Fleischmann |
| 2002/0115952 A1 | 8/2002 | Tumey |
| 2002/0120185 A1 | 8/2002 | Johnson |

(56) References Cited

U.S. PATENT DOCUMENTS

| | | |
|---|---|---|
| 2002/0143286 A1 | 10/2002 | Tumey |
| 2002/0150720 A1 | 10/2002 | Howard et al. |
| 2002/0161346 A1 | 10/2002 | Lockwood et al. |
| 2002/0183702 A1 | 12/2002 | Henley et al. |
| 2002/0198503 A1 | 12/2002 | Risk et al. |
| 2002/0198504 A1 | 12/2002 | Risk et al. |
| 2003/0014022 A1 | 1/2003 | Lockwood et al. |
| 2003/0014025 A1 | 1/2003 | Allen et al. |
| 2003/0021775 A1 | 1/2003 | Freeman |
| 2003/0040687 A1 | 2/2003 | Boynton et al. |
| 2003/0050594 A1 | 3/2003 | Zamierowski |
| 2003/0088202 A1 | 5/2003 | Gilman |
| 2003/0097086 A1 | 5/2003 | Gura |
| 2003/0108587 A1 | 6/2003 | Orgill et al. |
| 2003/0125649 A1 | 7/2003 | Mcintosh et al. |
| 2003/0144619 A1 | 7/2003 | Augustine |
| 2003/0171675 A1 | 9/2003 | Rosenberg |
| 2003/0175798 A1 | 9/2003 | Raees et al. |
| 2003/0208149 A1 | 11/2003 | Coffey |
| 2003/0212357 A1 | 11/2003 | Pace |
| 2003/0212431 A1 | 11/2003 | Brady et al. |
| 2003/0225347 A1 | 12/2003 | Argenta et al. |
| 2004/0019342 A1 | 1/2004 | Nagasuna et al. |
| 2004/0030304 A1 | 2/2004 | Hunt et al. |
| 2004/0039391 A1 | 2/2004 | Argenta et al. |
| 2004/0039415 A1 | 2/2004 | Zamierowski |
| 2004/0054338 A1 | 3/2004 | Bybordi et al. |
| 2004/0064132 A1 | 4/2004 | Boehringer et al. |
| 2004/0122434 A1 | 6/2004 | Argenta et al. |
| 2004/0127834 A1 | 7/2004 | Sigurjonsson et al. |
| 2004/0127862 A1 | 7/2004 | Bubb et al. |
| 2004/0127863 A1 | 7/2004 | Bubb et al. |
| 2004/0163278 A1 | 8/2004 | Caspers et al. |
| 2004/0167482 A1 | 8/2004 | Watson |
| 2004/0225208 A1 | 11/2004 | Johnson |
| 2004/0241214 A1 | 12/2004 | Kirkwood et al. |
| 2004/0249353 A1 | 12/2004 | Risk, Jr. et al. |
| 2005/0004534 A1 | 1/2005 | Lockwood et al. |
| 2005/0010153 A1 | 1/2005 | Lockwood et al. |
| 2005/0020955 A1 | 1/2005 | Sanders et al. |
| 2005/0028828 A1 | 2/2005 | Heaton et al. |
| 2005/0033214 A1 | 2/2005 | Cantor |
| 2005/0058694 A1 | 3/2005 | Nielsen |
| 2005/0059915 A1 | 3/2005 | Dunagan |
| 2005/0070835 A1 | 3/2005 | Joshi |
| 2005/0080372 A1 | 4/2005 | Nielsen et al. |
| 2005/0090787 A1 | 4/2005 | Risk et al. |
| 2005/0148913 A1 | 7/2005 | Weston |
| 2005/0186260 A1 | 8/2005 | Narini et al. |
| 2005/0222527 A1 | 10/2005 | Miller et al. |
| 2005/0261642 A1 | 11/2005 | Weston |
| 2005/0261643 A1 | 11/2005 | Bybordi et al. |
| 2006/0025727 A1 | 2/2006 | Boehringer et al. |
| 2006/0029650 A1 | 2/2006 | Coffey |
| 2006/0041247 A1 | 2/2006 | Petrosenko et al. |
| 2006/0069365 A1 | 3/2006 | Sperl et al. |
| 2006/0079852 A1 | 4/2006 | Bubb et al. |
| 2006/0100586 A1 | 5/2006 | Karpowicz |
| 2006/0100594 A1 | 5/2006 | Adams et al. |
| 2006/0116620 A1 | 6/2006 | Oyaski |
| 2006/0149170 A1 | 7/2006 | Boynton et al. |
| 2007/0010797 A1 | 1/2007 | Nishtala et al. |
| 2007/0038172 A1 | 2/2007 | Zamierowski |
| 2007/0055209 A1 | 3/2007 | Patel et al. |
| 2007/0118096 A1 | 5/2007 | Smith et al. |
| 2007/0141128 A1 | 6/2007 | Blott et al. |
| 2007/0167884 A1 | 7/2007 | Mangrum et al. |
| 2007/0179460 A1 | 8/2007 | Adahan |
| 2007/0185426 A1 | 8/2007 | Ambrosio et al. |
| 2007/0185463 A1 | 8/2007 | Mulligan |
| 2007/0219532 A1 | 9/2007 | Karpowicz et al. |
| 2007/0225663 A1 | 9/2007 | Watt et al. |
| 2007/0265585 A1 | 11/2007 | Joshi et al. |
| 2007/0265586 A1 | 11/2007 | Joshi et al. |
| 2008/0004549 A1 | 1/2008 | Anderson et al. |
| 2008/0004559 A1 | 1/2008 | Riesinger |
| 2008/0039759 A1 | 2/2008 | Holm et al. |
| 2008/0077091 A1 | 3/2008 | Mulligan |
| 2008/0082059 A1 | 4/2008 | Fink et al. |
| 2008/0108977 A1 | 5/2008 | Heaton et al. |
| 2008/0119802 A1 | 5/2008 | Riesinger |
| 2008/0167593 A1 | 7/2008 | Fleischmann |
| 2008/0183119 A1 | 7/2008 | Joshi |
| 2008/0188820 A1 | 8/2008 | Joshi |
| 2008/0208147 A1 | 8/2008 | Argenta et al. |
| 2008/0223378 A1 | 9/2008 | Henderson et al. |
| 2008/0306407 A1 | 12/2008 | Taylor |
| 2008/0306456 A1 | 12/2008 | Riesinger |
| 2009/0005746 A1 | 1/2009 | Nielsen et al. |
| 2009/0036873 A1 | 2/2009 | Nielsen et al. |
| 2009/0054855 A1 | 2/2009 | Blott et al. |
| 2009/0054856 A1 | 2/2009 | Mormino et al. |
| 2009/0069759 A1 | 3/2009 | Blott et al. |
| 2009/0105670 A1 | 4/2009 | Bentley et al. |
| 2009/0125004 A1 | 5/2009 | Shen et al. |
| 2009/0131888 A1 | 5/2009 | Joshi |
| 2009/0177135 A1 | 7/2009 | Rogers et al. |
| 2009/0192499 A1 | 7/2009 | Weston et al. |
| 2009/0198201 A1 | 8/2009 | Adahan |
| 2009/0216170 A1 | 8/2009 | Robinson et al. |
| 2009/0221977 A1 | 9/2009 | Blott et al. |
| 2009/0227968 A1 | 9/2009 | Vess |
| 2009/0227969 A1 | 9/2009 | Jaeb et al. |
| 2009/0234306 A1 | 9/2009 | Vitaris |
| 2009/0234307 A1 | 9/2009 | Vitaris |
| 2009/0234309 A1 | 9/2009 | Vitaris et al. |
| 2009/0240185 A1 | 9/2009 | Jaeb et al. |
| 2009/0240218 A1 | 9/2009 | Braga et al. |
| 2009/0254053 A1 | 10/2009 | Svensby et al. |
| 2009/0254054 A1 | 10/2009 | Blott et al. |
| 2009/0264837 A1 | 10/2009 | Adahan |
| 2009/0270820 A1 | 10/2009 | Johnson |
| 2009/0299251 A1 | 12/2009 | Buan |
| 2009/0299255 A1 | 12/2009 | Kazala, Jr. et al. |
| 2009/0299256 A1 | 12/2009 | Barta et al. |
| 2009/0299257 A1 | 12/2009 | Long et al. |
| 2009/0299306 A1 | 12/2009 | Buan |
| 2009/0299307 A1 | 12/2009 | Barta et al. |
| 2009/0299341 A1 | 12/2009 | Kazala, Jr. et al. |
| 2009/0299342 A1 | 12/2009 | Cavanaugh, II et al. |
| 2009/0306580 A1 | 12/2009 | Blott et al. |
| 2009/0312723 A1 | 12/2009 | Blott et al. |
| 2009/0312728 A1 | 12/2009 | Randolph et al. |
| 2009/0326487 A1 | 12/2009 | Vitaris |
| 2010/0010477 A1 | 1/2010 | Augustine et al. |
| 2010/0036334 A1 | 2/2010 | Heagle et al. |
| 2010/0036367 A1 | 2/2010 | Krohn |
| 2010/0042074 A1 | 2/2010 | Weston et al. |
| 2010/0063483 A1 | 3/2010 | Adahan |
| 2010/0063484 A1 | 3/2010 | Heagle |
| 2010/0069858 A1 | 3/2010 | Olson |
| 2010/0069863 A1 | 3/2010 | Olson |
| 2010/0087767 A1 | 4/2010 | McNeil |
| 2010/0100063 A1 | 4/2010 | Joshi et al. |
| 2010/0100075 A1 | 4/2010 | Weston et al. |
| 2010/0106114 A1 | 4/2010 | Weston et al. |
| 2010/0121286 A1 | 5/2010 | Locke et al. |
| 2010/0122417 A1 | 5/2010 | Vrzalik et al. |
| 2010/0125258 A1 | 5/2010 | Coulthard et al. |
| 2010/0150991 A1 | 6/2010 | Bernstein |
| 2010/0160879 A1 | 6/2010 | Weston |
| 2010/0185163 A1 | 7/2010 | Heagle |
| 2010/0207768 A1 | 8/2010 | Pidgeon et al. |
| 2010/0249733 A9 | 9/2010 | Blott |
| 2010/0262090 A1 | 10/2010 | Riesinger |
| 2010/0268198 A1 | 10/2010 | Buan et al. |
| 2010/0274207 A1 | 10/2010 | Weston |
| 2010/0278518 A1 | 11/2010 | Gordon |
| 2010/0280468 A1 | 11/2010 | Haggstrom et al. |
| 2010/0286635 A1 | 11/2010 | Watson, Jr. |
| 2010/0286638 A1 | 11/2010 | Malhi |
| 2010/0298866 A1 | 11/2010 | Fischvogt |
| 2010/0305490 A1 | 12/2010 | Coulthard et al. |
| 2010/0305524 A1 | 12/2010 | Vess et al. |

(56) References Cited

U.S. PATENT DOCUMENTS

| | | |
|---|---|---|
| 2010/0318043 A1 | 12/2010 | Malhi et al. |
| 2010/0324510 A1 | 12/2010 | Andresen et al. |
| 2010/0324516 A1 | 12/2010 | Braga et al. |
| 2010/0331797 A1 | 12/2010 | Patet et al. |
| 2011/0004172 A1 | 1/2011 | Eckstein et al. |
| 2011/0009835 A1 | 1/2011 | Blott |
| 2011/0015593 A1 | 1/2011 | Svedman et al. |
| 2011/0028918 A1 | 2/2011 | Hartwell |
| 2011/0028921 A1 | 2/2011 | Hartwell et al. |
| 2011/0034892 A1 | 2/2011 | Buan |
| 2011/0046584 A1 | 2/2011 | Haggstrom et al. |
| 2011/0054421 A1 | 3/2011 | Hartwell |
| 2011/0054422 A1 | 3/2011 | Locke et al. |
| 2011/0054423 A1 | 3/2011 | Blott et al. |
| 2011/0087176 A2 | 4/2011 | Blott |
| 2011/0087178 A2 | 4/2011 | Weston |
| 2011/0087180 A2 | 4/2011 | Weston |
| 2011/0092927 A1 | 4/2011 | Wilkes et al. |
| 2011/0092958 A1 | 4/2011 | Jacobs |
| 2011/0105963 A1 | 5/2011 | Hu et al. |
| 2011/0106030 A1 | 5/2011 | Scholz |
| 2011/0112492 A1 | 5/2011 | Bharti et al. |
| 2011/0118683 A1 | 5/2011 | Weston |
| 2011/0130712 A1 | 6/2011 | Topaz |
| 2011/0172615 A2 | 7/2011 | Greener et al. |
| 2011/0230849 A1 | 9/2011 | Coulthard et al. |
| 2011/0251567 A1 | 10/2011 | Blott et al. |
| 2011/0282309 A1 | 11/2011 | Adie et al. |
| 2012/0053538 A1 | 3/2012 | Blott et al. |
| 2012/0109084 A1 | 5/2012 | Blott et al. |
| 2012/0157942 A1 | 6/2012 | Weston |
| 2014/0283847 A1 | 9/2014 | Sanders et al. |

FOREIGN PATENT DOCUMENTS

| | | |
|---|---|---|
| CA | 2 390 513 | 5/2001 |
| CA | 2 121 688 | 7/2001 |
| CA | 2 408 305 | 11/2001 |
| CA | 2 458 285 | 3/2003 |
| CA | 2 157 772 | 9/2003 |
| DE | 2 809 828 | 9/1978 |
| DE | 3 935 818 | 5/1991 |
| DE | 4 012 232 | 10/1991 |
| DE | 198 44 355 | 4/2000 |
| EP | 0 020 662 | 7/1984 |
| EP | 0 355 186 | 2/1990 |
| EP | 0 777 504 | 10/1998 |
| EP | 0 782 421 | 7/1999 |
| EP | 1 897 569 | 8/2002 |
| EP | 0 708 620 | 5/2003 |
| EP | 1 088 569 | 8/2003 |
| EP | 1 440 667 | 3/2006 |
| EP | 1 284 777 | 4/2006 |
| EP | 1 171 065 | 3/2007 |
| EP | 1 476 217 | 3/2008 |
| EP | 1 121 163 | 11/2008 |
| EP | 2 098 257 | 9/2009 |
| FR | 1163907 | 10/1958 |
| GB | 114754 | 4/1918 |
| GB | 641061 | 8/1950 |
| GB | 1224009 | 3/1971 |
| GB | 1549756 | 8/1979 |
| GB | 2195255 | 4/1988 |
| GB | 2378392 | 2/2003 |
| GB | 2415908 | 1/2006 |
| JP | 2003-165843 | 6/2003 |
| SU | 1251912 A1 | 4/1983 |
| WO | WO 1984/01904 | 5/1984 |
| WO | WO 1990/11795 | 10/1990 |
| WO | WO 1991/00718 | 1/1991 |
| WO | WO 1992/20299 | 11/1992 |
| WO | WO 1996/05873 | 2/1996 |
| WO | WO 1999/01173 | 1/1999 |
| WO | WO 2000/07653 | 2/2000 |
| WO | WO 2000/50143 | 8/2000 |
| WO | WO 2000/59424 | 10/2000 |
| WO | WO 2001/19430 | 3/2001 |
| WO | WO 02/091964 | * 5/2001 |
| WO | WO 2001/34223 | 5/2001 |
| WO | WO 2001/37922 | 5/2001 |
| WO | WO 2001/85248 | 11/2001 |
| WO | WO 2001/93793 | 12/2001 |
| WO | WO 2002/083046 | 10/2002 |
| WO | WO 2002/091964 | 11/2002 |
| WO | WO 2002/092783 | 11/2002 |
| WO | WO 2003/045492 | 6/2003 |
| WO | WO 2003/057307 | 7/2003 |
| WO | WO 2003/092620 | 11/2003 |
| WO | WO 2004/024300 | 3/2004 |
| WO | WO 2004/037334 | 5/2004 |
| WO | WO 2005/025666 | 3/2005 |
| WO | WO 2005/051461 | 6/2005 |
| WO | WO 2005/070480 | 8/2005 |
| WO | WO 2005/082435 | 9/2005 |
| WO | WO 2007/024230 | 3/2007 |
| WO | WO 2007/030601 | 3/2007 |
| WO | WO 2008/133170 | 11/2008 |
| WO | WO 2009/066105 | 5/2009 |
| WO | WO 2009/066106 | 5/2009 |
| WO | WO 2010/121186 | 10/2010 |
| WO | WO 2012/022484 | 2/2012 |

OTHER PUBLICATIONS

U.S. Appl. No. 10/599,720, filed Oct. 6, 2006, Blott et al.
U.S. Appl. No. 12/192,000, filed Apr. 14, 2008, Hartwell et al.
U.S. Appl. No. 12/192,000, filed Aug. 14, 2008, Hartwell et al.
Achterberg, V., Ph.D., Hydroactive dressings and serum proteins: an in vitro study, Journal of Wound Care, February, vol. 5, No. 2, 1996 (pp. 79-82).
Argenta, Louis C., et al., "Vacuum-Assisted Closure: A New Method for Wound Control and Treatment; Clinical Experience", Ann Plas Surg 1997;38:563-577 (Dec. 10, 1996).
Aubrey, D.A. et al., Treatment of the Perineal Wound after Proctectomy by Intermittent Irrigation, Arch. Surg., Oct. 1984, 119, 1141-1144.
Bagautdinov, N.A., "Variant of External Vacuum Aspiration in the Treatment of Purulent Diseases of Soft Tissues," in current Problems in Modern Clinical Surgery: Interdepartmental Collection, edited by V. Ye. Volkov et al. (Chuvashia State University, Cheboksary, USSR 1986) pp. 94-96 (with English translation).
Biblehimer, Helen L., "Dealing With a Wound that Drains 1.5 Liters a Day," RN, Aug. 1986, pp. 21-23, USA.
Bier, A., Hyperemia as a Therapeutic Agent, Ed. Dr. Gustavus M. Blech, A. Robertson & Co., Chicago 1905.
Brubacher, Lynda L., "To Heal a Draining Wound", RN, Mar. 1982, pp. 30-35, USA.
Bucalo et al. "Inhibition of Cell Proliferation by Chronic Wound Fluid." Wound Repair and Regeneration. Miami, 1993. pp. 181-186.
Chariker, M.E., et al, "Effective Management of Incisional and Cutaneous Fistulae with Closed Suction Wound Drainage," Contemporary Surgery. Jun. 1989, pp. 59-63, vol. 34 USA.
Chintamani, et al., "Half versus full vacuum suction drainage after modified radical mastectomy for breast cancer—a prospective randomized clinical trial", Research Article (Jan. 27, 2005), 1-5.
Costunchenok, B.M., et al., Effect of Vacuum on Surgical Purulent Wounds, Vestnik Chirurgia, Sep. 18-20, 1986 (in Russian with English translation).
Davydov et al. "Pathogenic Mechanism of the Effect of Vacuum Therapy on the Course of the Wound Process" pp. 43-46 (Dec. 1990).
Davydov, Yu A., et al., "Concepts for Clinical Biological Management of the Wound Process in the Treatment of Purulent Wounds Using Vacuum Therapy", The Kremlin Papers: Perspectives in Wound Care, Russian Journal: Vestnik Khirurgii, BlueSky Publishing, La Costa, California (2004), 15-17.
Davydov, Yu A., et al., "The Bacteriological and Cytological Assessment of Vacuum Therapy of Purulent Wounds", The Kremlin Papers: Perspectives in Wound Care, Russian Journal: Vestnik Khirurgii, BlueSky Publishing, La Costa, California (2004), 11-14.

(56) References Cited

OTHER PUBLICATIONS

Davydov, Yu A., et al., "Vacuum Therapy in the Treatment of Purulent Lactation Mastitis", The Kremlin Papers: Perspectives in Wound Care, Russian Journal: Vestnik Khirurgii, BlueSky Publishing, La Costa, California (2004), 5-7.
De Lange, M.Y., et al., "Vacuum-Assisted Closure: Indications and Clinical Experience", Eur J Plast Surg (2000) 2;178-182 (Feb. 9, 2000).
Dilmaghani et al., "A Method for Closed Irrigation and Suction Therapy in Deep Wound Infections," Journal of Bone and Joint Surgery, 1969, vol. 51-A, No. 2, pp. 323-342.
Fleischmann et al., Vacuum Sealing: Indication, Technique, and Results, Eur J Orthop Surg Traumatol, (1995) 5:37-40.
Fleischmann, W. Wund Forum Spezial, "Vakuumversiegelung zur Behandlung von Problemwunden" (with English translation: Vacuum Sealing for Treatment of Problematical Wounds), *IHW* '94, 6 pages.
Garcia-Rinaldi, R., et al., Improving the Efficiency of Wound Drainage Catheters, *Amer. Journ. of Surg.*, Sep. 1975, 130, 372-373.
Hartz, R.S., et al., Healing of the Perineal Wound, Arch. Surg., Apr. 1980, 115, 471-474.
Health Technology, Literature R., "Vacuum Assisted Closure Therapy for Wound Care", Health Technology Literature Review (Dec. 2004), 3-59.
Jeter, K. et al., "Managing Draining Wounds and Fistulae: New and Established Methods" Chronic Wound Care pp. 240-246, 1990.
Johnson, F.E., An Improved Technique for Skin Graft Placement using a Suction Drain, *Surgery, Gynecology & Obstetrics*, Dec. 1984, 159(6), 584-585.
KCI, Inc. If It's Not V.A.C. Therapy, It's Not Negative Pressure Wound Therapy, *KCI Brochure*, Jan. 2005, 1-5.
Khirugii, Vestnik, "A Collection of Published Studies Complementing the Research and Innovation of Wound Care", The Kremlin Papers, Perspectives in Wound Care, Russian Medical Journal, Vestnik Khirugii, Blue Sky Publishing (2004), 2-17.
Kostiuchenok, B. M., et al., "The Vacuum Effect in the Surgical Treatment of Purulent Wounds", The Kremlin Papers: Perspectives in Wound Care, Russian Journal: Vestnik Khirurgii, BlueSky Publishing, La Costa, California (2004), 3-4.
Landes, R.R. and I. Melnick, An Improved Suction Device for Draining Wounds, *Arch. Surg.*, May 1972, 104, p. 707.
Linden van der, Willem, Randomized Trial of Drainage After Cholecystectomy, Modern Operative Techniques, Voluje 141, Feb. 1981, pp. 289-294.
McFarlane, R. M., "The Use of Continuous Suction Under Skin Flaps", F.R.C.S.(c), vol. 1, pp. 77-86 (1958).
McLaughlan, James, Sterile Microenvironment for Postoperative Wound Care, The Lancet, pp. 503-504, Sep. 2, 1978.
Meyer, Weight-Loaded Syringes as a Simple and Cheap Alternative to Pumps for Vacuum-Enhanced Wound Healing, Plastic and Reconstructive Srug., Jun. 2005, 2174-2176 (Correspondence).
Morykwas, Michael J., et al., "Vacuum-Assisted Closure: A New Method for Wound Control and Treatment: Animal Studies and Basic Foundation", Ann Plast Surg 1997;38:553-562 (Dec. 10, 1996).
Nakayama, Y., et al., "A New Method for the Dressing of Free Skin Grafts", Plastic and Reconstructive Surgery, Dec. 1990 pp. 1216-1219, UK.
Nursing75, Wound Suction: Better Drainage with Fewer Problems, Nursing, vol. 5, No. 10, Oct. 1975, pp. 52-55.
Ramirez, O.M., et al., Optimal Wound Healing under Op-Site Dressing, Ideas and Innovations, 73(3), pp. 474-475.
Ranson, John H. M.D., Safer Intraperitoneal Sump Drainage, Surgery Gynnecology and Obstetrics, pp. 841-842, 1973 vol. 137.
Sames, C.P., Sealing of Wounds with Vacuum Drainage, *Br. Med. Journ.*, Nov. 5, 1977, p. 1223, Correspondence.

Solovev, V. A., et al., "The Method of Treatment of Immature External Fistulas in the Upper Gastrointestinal Tract—Guidelines" USSR Ministry of Health, S. M. Kirov Gorky State Medical Institute, 1987 (with English translation).
Solovev, V.A. "Treatment and Prevention of Suture Failures after Gastric Resection" (Dissertation Abstract) (S.M. Kirov Gorky State Medical Institute, Gorky USSR 1988).
Stewart, Joanne, Ph.D., World Wide Wounds—Next generation of products for wound management—2002 (13 pages).
Svedman, P., "Irrigation Treatment in Split-Thickness Skin Grafting of Intractable Leg Ulcers," Scand J. Plast. Reconst. Surg., 19:211-213, 1985.
Svedman, P., "Irrigation Treatment of Leg Ulcers," The Lancet, Sep. 1983, 532-34.
Svedman, P., A Dressing Allowing Continuous Treatment of a Biosurface, IRCS Med. Science: Biomed. Tech.; Clinic. Med.; Surg. and Transplantation, 1979, 7, p. 221.
Svedman, P., et al., "A Dressing System Providing Fluid Supply and Suction Drainage Used for Continuous or Intermittent irrigation," Annals of Plastic Surgery, vol. 17, No. 2, Aug. 1986, pp. 125-133.
Swift, et al, "Quorum Sensing in *Aeromonas hydrophila* and *Aeromonas salmoncida*: Identification of LuxRI Homologs AhyRl and AsaRI and Their Cognate N-Acylhomoserine Lactone Signal Molecules," J. Bacteriol., 179(17):5271-5281 (1997).
Teder and Svedman et al., "Continuous Wound Irrigation in the Pig," Journal of Investigative Surgery, 1990, vol. 3, pp. 399-407.
Tribble, David E. M.D., An Improved Sump Drain-Irrigation Device of Simple Construction, Archives of Surgery New York, pp. 511-513, 1972 vol. 105.
Usupov, Y. N., et al., "Active Wound Drainage", The Kremlin Papers: Perspectives in Wound Care, Russian Journal: Vestnik Khirurgii, BlueSky Publishing, La Costa, California (2004), 8-10.
Venturi, Mark L., "Mechanisms and Clinical Applciations of the Vacuum-Assisted Closure (VAC) Device", Am J Clin Dermatol (2005) 693, 185-194; Review Article (2005), 185-194.
Vijanto, J. and J. Raekallio, Local Hyperalimentation of Open Wounds, Br. J. surg., 1976, 63, 427-430.
Wackenfors, A., et al., Effects of Vacuum-Assisted Closure Therapy on Inguinal Wound Edge Microvascular Blood Flow, *Wound Rep. Reg*, 2004, 12, 600-606.
Webb, New Techniques in Wound Management: Vacuum-Assisted Wound Closure, Journal of the American Academy of Orthopadic Surgeons, v. 10, No. 5, pp. 303-311, Sep. 2002.
Webster's Revised Unabridged Dictionary, published 1913 by C. & G. Merriam Co., definition of Flapper Valve, downloaded from Free Online Dictionary.
Westaby, S., et al., "A Wound Irrigation Device", The Lancet, Sep. 2, 1978, pp. 503-504.
Wooding-Scott, Margaret, et al., "No Wound is Too Big for Resourceful Nurses," RN Dec. 1988, pp. 22-25 USA.
Wound Suction, Nursing, Oct. 1975, USA pp. 52-53.
Wu, W.S. et al. Vacuum therapy as an intermediate phase in wound closure: a clinical experience, Eur J Past Surg (2000) 23: 174-177.
Kendall ULTEC Hydrocolloid Dressing (4"x4"), product ordering page, web page downloaded Jul. 13, 2014.
Protz, Kerstin: "Modern Wundauflagen unterstutzen Heilungsprozess", Wundversorgung: Indikation and Anwendung, Geriatrie Journal, Apr. 2005, pp. 3333-3339, with translation.
Valenta, A.L., Using the Vacuum Dressing Alternative for Difficult Wounds, AIN, Apr. 1994, 44-45.
Meyer, W. et al., Bier's Hyperemic Treatment, published 1908, W. B. Saunders Company, pp. 44-65, in 12 pages.
Meyer, D. et al., "Weight-Loaded Syringes as a Simple and Cheap Alternative to Pumps for Vacuum-Enhanced Wound Healing", Plastic and Reconstructive Surg., Jun. 2005, 2174-2176 (Correspondence).

* cited by examiner

NEGATIVE PRESSURE WOUND THERAPY DEVICE

RELATED APPLICATIONS

This application claims priority to U.S. Nonprovisional application Ser. No. 14/179,893, filed Feb. 13, 2014, which claims priority to U.S. Nonprovisional application Ser. No. 12/762,149, filed Apr. 16, 2010, which claims priority to U.S. Provisional Application No. 61/212,947 filed on Apr. 17, 2009. The entireties of which is the aforementioned applications are incorporated herein.

TECHNICAL FIELD

The present invention relates, in general, to a device and method for wound therapy that is capable of treating a variety of chronic and acute wound types, including, but not limited to, infection wounds, venous ulcers, arterial ulcers, diabetic ulcers, burn wounds, post amputation wounds, surgical wounds, and the like. Specifically, the present disclosure is related to wound treatment devices for a wound, for example, on a foot and methods that utilize a negative pressure therapy device for treatment of same.

BACKGROUND

Negative pressure therapy has been one method used for the treatment of a variety of wounds by practitioners in the art. Conventional negative pressure therapy devices are generally large in size and often require the use of complicated equipment such as suction pumps, vacuum pumps and complex electronic controllers. Additionally, U.S. Patent Pre-Grant Publication Nos. 2007/0265585 and 2007/0265586, the entire contents of which are herein incorporated by reference, also disclose negative pressure therapy devices.

Since the negative pressure therapy devices utilize negative pressure, it is desirable to minimize the opportunity for leaks in same, so as to prevent increased damage to the patient and/or wound, or unnecessarily prolonged damage to the patient and/or wound.

With respect to a wound located on a foot, there are specific drawbacks involving the time needed to deploy a conventional negative pressure wound therapy device. In addition, due to the shape of a foot, obtaining a satisfactory seal over the wound can be problematic and contribute to the increased time needed to deploy a conventional negative pressure wound therapy device.

Other wound locations on a patient's body may present drawbacks and problems similar to those associated with a wound on a foot. Therefore, nothing in this description should be meant to restrict the present invention to be used only with a wound on a foot. Rather, as would be appreciate by one of ordinary skill in the art, the benefits of the present invention can be appreciated and utilized through use of with any wound that is susceptible to negative pressure wound treatment.

While current negative pressure wound therapy devices are presumably effective for their intended purposes, there is a need for a device that allows a medical professional flexibility in placing the negative pressure wound therapy device, so as to provide the patient with a comfortable and efficient treatment.

BRIEF SUMMARY

Generally, a negative pressure wound therapy device according to one embodiment of the present invention includes a housing material having a first side and a second side, a gasket disposed on the first side of the housing material, an adhesive disposed on the first side of the housing material, a port disposed through the housing material, a liner disposed on the adhesive, a non-woven absorption material, and, a wound interface layer surrounding the non-woven absorption material.

The port may be configured to prevent exudates from flowing through the port towards the pump (which supplies the negative pressure).

The gasket is sized and configured such that when the housing material is folded back upon itself to surround a wound on an appendage, at least a first portion of the gasket is adhered to a second portion of the gasket.

In another embodiment of the present invention, the present invention provides a kit for a negative pressure wound therapy device including a housing material having a first side and a second side, a gasket disposed on the first side of the housing material, an adhesive disposed on the first side of the housing material, a port disposed through the housing material, and a liner disposed on the adhesive. The kit may also include a non-woven absorption material that can be secured to the housing by the adhesive and disposed on a wound after removal of the liner.

The kit may also include a wound interface layer to be disposed between the non-woven absorption material and the wound.

Alternatively, the kit may further include a wound interface layer surrounding the non-woven absorption material.

The kit may also include a second liner disposed on first side of the housing material.

The kit further may include a stiffener disposed on second side of the housing material.

In another embodiment the port may be configured to prevent exudates from flowing through the port.

In still another embodiment, the kit may include tubing and a pump.

In another embodiment of the invention, the invention provides a method of treating a wound with negative pressure wound therapy that includes the steps of disposing a non-woven absorption material above a wound, removing at least a portion of a liner from a housing material having a first side with an adhesive and a port disposed through the housing material, positioning the housing material around an appendage of the patient having the wound, folding the housing material, positioning the port adjacent the non-woven absorption material, sealing the housing material to the appendage, and, applying negative pressure to the wound.

The method may further include the step of disposing a wound interface layer in between the non-woven absorption material and the wound.

The method may include wherein the housing material is sealed to the appendage such that a first portion of the gasket is adhered to a second portion of the gasket. Additionally, a third portion of the gasket may be adhered to a fourth portion of the gasket.

The method may further include wherein the step of disposing the wound interface layer in between the non-woven absorption material and the wound includes the step of surrounding the non-woven absorption material with the wound interface layer.

The method may further include removing a second liner and/or a stiffener from the housing material.

The method may also include folding the housing material such that a portion of the housing material is folded onto a second portion of the housing material.

The folding of the housing material may be in a direction that is perpendicular to a longitudinal axis of the appendage, or it may be in a direction that is parallel to a longitudinal axis of the appendage.

The method may include removing at least a portion of a liner from a housing material includes removing all of the liner.

The method may also include collecting and retaining exudates within the non-woven absorption material.

The method may further include preventing exudates from flowing through the port.

A device and method as described herein is believed to provide a variety of benefits to aid in the treatment of a wound with negative pressure wound therapy.

First, such a device and method would provide for a device to be applied with a multitude of configurations when compared with conventional devices that come completely pre-arranged. In other words, a medical professional is able to determine the best location for the wound interface layer and non-woven absorption material and position those portions of the devices separate and apart from the housing material with the port. This will increase the ability to utilize such a device and method on wounds that, because of the location of the wound, are difficult to effectively treat with negative pressure wound therapy.

In addition, the design is believed to provide an improved seal compared with some of the negative pressure wound therapy devices that are currently commercially available. The improved seal results in less time needed to confirm that the device has obtained overall satisfactory seal and less time adjusting the device to eliminate gaps and other spaces that allow negative pressure to dissipate and result in the device performing with a reduced efficiency.

In addition, since the device includes the gasket and the non-woven absorption material, the device can be used with a pump that is much smaller than conventionally used pumps. This is because the non-woven absorption material absorbs the exudates. Therefore, the pump does not need a large container to collect the exudates. In addition, since the device provides a satisfactory seal, the pump can be operated with small batteries, such as AA batteries.

Other benefits of the present invention will become readily apparent to those of ordinary skill in the art with this disclosure and the attached drawings before them.

BRIEF DESCRIPTION OF THE DRAWINGS

The present invention will become more fully apparent from the following description and appended claims, taken in conjunction with the accompanying drawings. Understanding that the accompanying drawings depict only typical embodiments, and are, therefore, not to be considered to be limiting of the scope of the present disclosure, the embodiments will be described and explained with specificity and detail in reference to the accompanying drawings as provided below.

DETAILED DESCRIPTION

Figure 1:
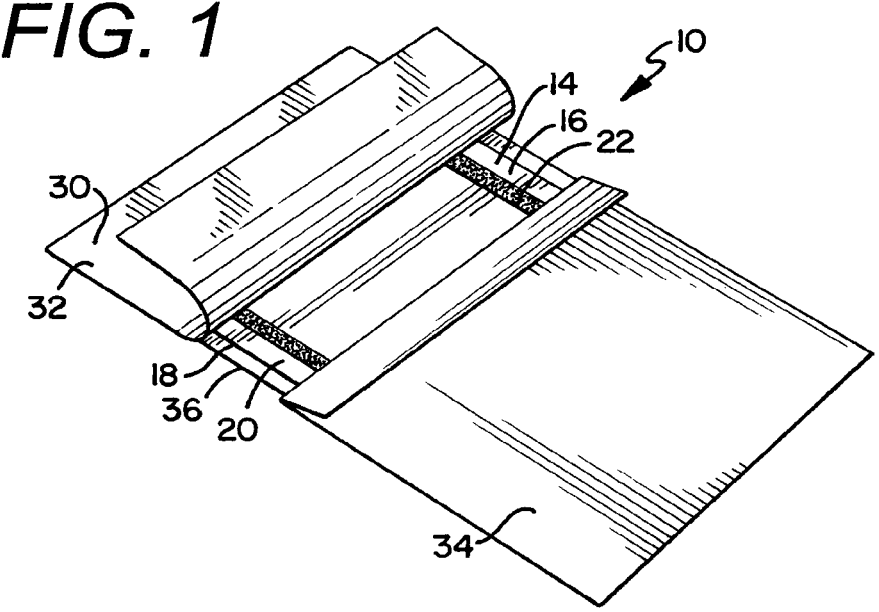
FIG. 1 is a top perspective view of a device according to the present invention.
Figure 2:
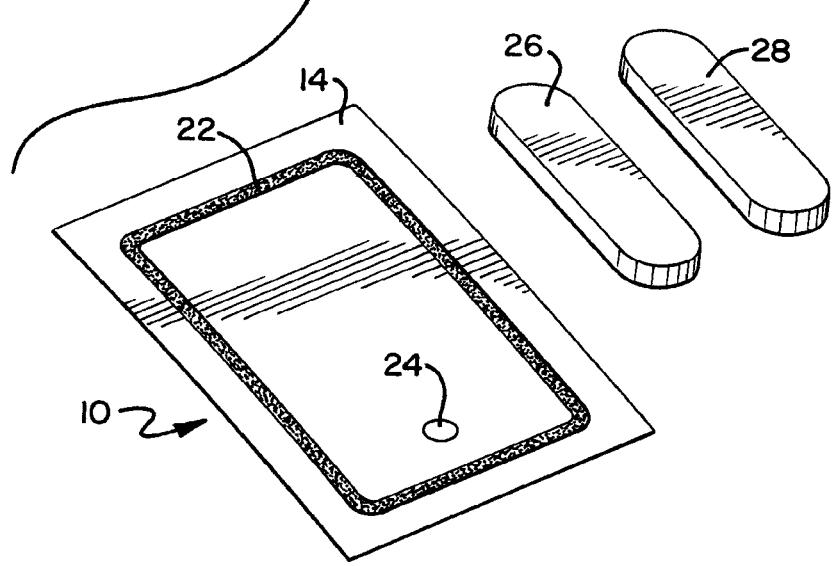
FIG. 2 is another top perspective view of a device according to the present invention.
Figure 3:
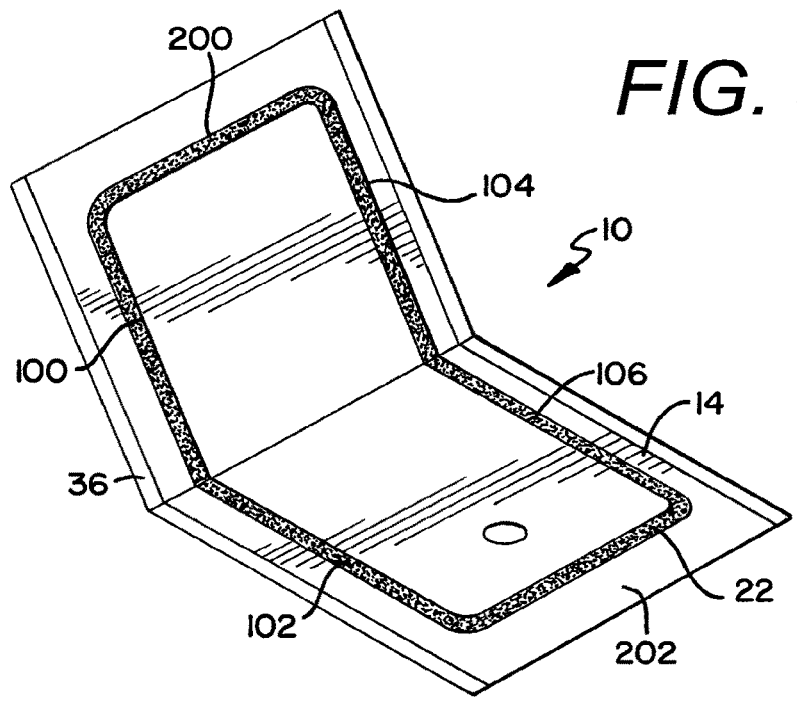
FIG. 3 is another top perspective view of a device according to the present invention.
Figure 4:
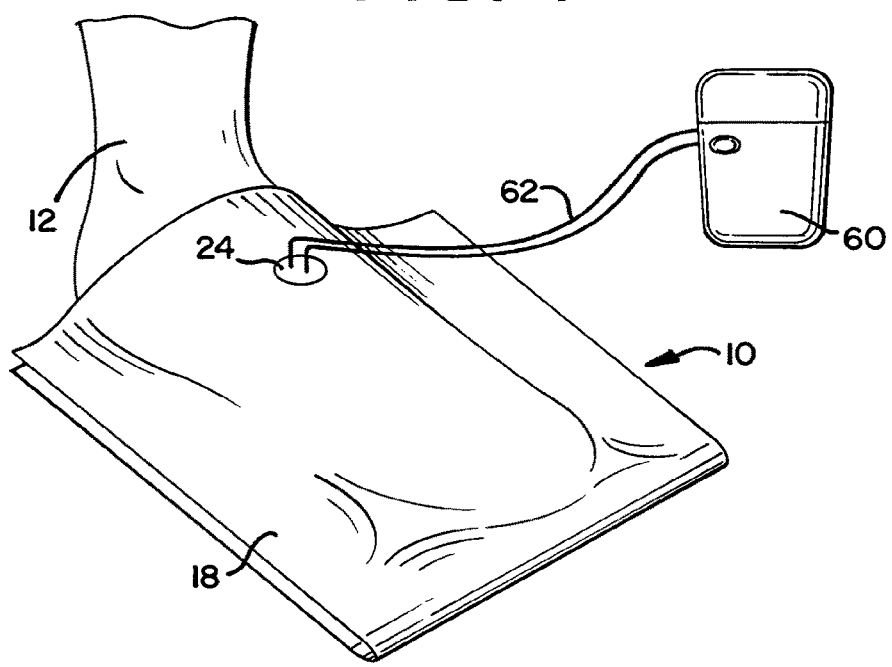
FIG. 4 is another top perspective view of a device according to the present invention.

It will be readily understood that the components of the embodiments as generally described and illustrated in the Figures herein could be arranged and designed in a wide variety of different configurations. Thus, the following more detailed description of various embodiments, as represented in the Figures, is not intended to limit the scope of the present disclosure, but is merely representative of various embodiments. While the various aspects of the embodiments are presented in drawings, the drawings are not necessarily drawn to scale unless specifically indicated.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention can be practiced without one or more of the specific features or advantages of a particular embodiment. In other instances, additional features and advantages may be recognized in certain embodiments that may not be present in all embodiments of the invention.

As shown in the attached drawings, a negative pressure wound therapy device 10 for treating a wound on, for example, a foot 12 according to one or more embodiments of the present includes a housing material 14 with a first side 16 and a second side 18. The housing material 14 is flexible such that it can be folded. In addition, it should be comprised of a material that will allow negative pressure to be provided to a wound disposed underneath the housing material 14.

Around at least a portion of the periphery 20 of the first side 16 housing material 14 is a gasket 22.

It is preferred that the gasket 22 is a hydro-gel material. Incorporated herein by reference is U.S. Pre Grant Publication No. 2009/0299251, assigned to the applicant, that provides additional details and disclosure regarding the use of a gasket in a negative pressure wound therapy device.

The gasket 22 is sized and configured such that when the housing material is folded back upon itself to surround a wound on an appendage, at least a first portion 100 of the gasket 22 is adhered to a second portion 102 of the gasket 22. If the appendage is a foot 12, for example, a third portion 104 of the gasket 22 may also be adhered to a fourth portion 106 of the gasket 22. In other words, on both sides of the foot 12, the gasket 22 adheres to itself when the housing material 14 is folded to surround the wound on an appendage.

The gasket 22 has a thickness, and it is contemplated that the thickness of the gasket 22, for example, is between 3 to 5 mils and the width of the gasket 22 is approximately ⅜ of an inch.

In one embodiment of the invention the gasket 22 may be a hydrogel. Such materials are currently available from Katecho, in Des Moines, Iowa (USA). It is preferred that the gasket 22 be a material that be biocompatible with skin. In addition the gasket 22 material should mildly adhere to the skin, but not adhere to the skin in the same manner as the adhesive on the housing material 14. In addition, the gasket 22 material should be mildly flowable. Furthermore, the gasket 22 material should be non-reactive to normal medical device sterility processes. Another contemplated material is a silicone gel; however, it is currently believed to be too cost prohibitive to utilize the silicone gel.

It is contemplated that one of ordinary skill in the art will appreciate that other shapes and designs of the housing material 14 and gasket 22 could be used. In addition, it is contemplated that other configurations of the gasket 22 could be used. For example, the gasket 22 could be comprised of a plurality of pieces arranged such that some of the pieces will adhere to other pieces when the housing material is folded.

An adhesive (not shown) is also located on at least a portion of the first side 16 of the housing material 14.

The wound therapy device 10 also includes a port 24 that allows the device 10 to communicate with a pump 60 via tubing 62. The port 24 is configured so that it projects outward of the second side 18 of the housing material 14. It is preferred, but not required, that the pump 60 be a pump such as those described in U.S. Pat. Pre Grant Publication No. 2009/0299306, the entirety of which is incorporated herein by reference. It is contemplated that the port 24 is configured to prevent exudates and/or liquids removed from the wound from flowing through the port 24 and contaminating the pump 60.

Before use, the device 10 is stored with a liner 30 disposed on the first side 16 of the housing material 14. It is preferred that the liner 30 include a first portion 32 and a second portion 34. Disposed on the second side 18 of the housing 14 may be a stiffener 36 to provide the device 10 with temporary rigidity. The stiffener 36 may be removably attached to the second side of the housing 14 with an adhesive and functions to provide the flexible housing material 14 with some rigidity.

Separate from the housing material 14, the wound therapy device 10 (and kit for same) also includes a non-woven absorption material 26. The non-woven absorption material 26 will absorb liquids and exudates from the wound and it will facilitate communication of negative pressure from the port 24 to the wound. The non-woven absorption material 26 may comprise any number of different materials that are capable of absorbing the liquid and exudates removed from the wounds, while at the same time allowing negative pressure to be communicated to the wound from the pump 60.

The device 10 (and kit) also includes a wound interface layer 28. The wound interface layer 28 may be, for example Silverlon®. The wound interface layer 28 may surround the non-woven absorption material 26 so that it forms one piece. Alternatively, the wound interface layer 28 may be provided as a completely separate piece.

The wound interface layer 28 and non-woven absorption material 26 are included in the kit, but separate from the housing material 14 with liner 30. In other words, the wound interface layer 28 and non-woven absorption material 26 are not attached to the housing material 14. Unlike conventional devices and kits, this configuration will allow the wound interface layer 28 and non-woven absorption material 26 to be positioned independent of the housing material 14. In turn, this will allow for an unlimited amount of different configurations.

The device 10 (and kit) will now be described in relation to a method of using same.

A physician or other person will position the non-woven absorption material 26 above the wound on, for example, a foot 12. A second piece (not shown) of non-woven absorption material 26 can be used if the wound is disposed in a position that would result in the port being in a position that is uncomfortable for the patient, or could easily be damaged. The non-woven absorption material 26 will allow for the communication of negative pressure from the pump 60 to the wound, and therefore, it should be placed and arranged such that it extends from the wound to the port 24. This also allows for configurations where the port 24 is to be placed a distance from the wound.

Prior to placement of the non-woven absorption material 26, the wound interface layer 28 may be positioned between the wound and non-woven absorption material 26. In the embodiments where the wound interface layer 28 surrounds the non-woven absorption material 26, this step will occur upon the placement of the non-woven absorption material 26.

After placement of the non-woven absorption material 26, the first portion 32 of the liner 30 may be removed. Alternatively, if a liner 30 comprising a single piece is used, only a portion of the liner 30 is preferably removed.

The patient's foot 12 may then be placed on the device 10. The second portion 34 of the liner 30 may then be removed. Again, if a singularly pieced liner 30 is used, the remaining portion of the liner 30 can be removed. Alternatively, the entire liner may be removed.

The device 10 may then be folded onto itself to seal around the wound, so that a first portion 200 of the housing material 14 is folded back onto a second portion 202 of a housing material 14. It is preferred that the folding be relatively perpendicular to the longitudinal axis of the patient's foot 12, but it could also be parallel with the longitudinal axis of the foot 12 and still be within the scope of the present invention. Again, in order to allow for communication of negative pressure from the pump 60 to the wound, it is necessary that the port 24 be disposed above a portion of the non-woven absorption material 26.

As mentioned above, with the folding of the housing material, at least a first portion 100 of the gasket 22 will be folded back onto a second portion 102 of the gasket 22 and adhered thereto. And, a third portion 104 of the gasket 22 may also be folded back and adhered to a fourth portion 106 of the gasket 22. This is believed to allow the device to provide sufficient negative pressure to the wound and provide a sufficient seal of the device.

The stiffener 36 may then be removed and any excess portions of the housing material 14 may be folded, for example, under the foot 12. The port 24 may be connected with tubing 62 to the pump 60. The pump 60 will provide negative pressure which will remove exudates and liquid from the wound. The liquid and exudates will be absorbed and retained in the non-woven absorption material 26.

Without further elaboration, it is believed that one skilled in the art can use the preceding description to utilize the present disclosure to its fullest extent. The examples and embodiments disclosed herein are to be construed as merely illustrative and not a limitation of the scope of the present disclosure in any way. It will be apparent to those having skill in the art that changes may be made to the details of the above-described embodiments without departing from the underlying principles of the disclosure provided herein. In other words, various modifications and improvements of the embodiments specifically disclosed in the description above are within the scope of the appended claims. Note that elements recited in means-plus-function format are intended to be construed in accordance with 35 U.S.C. § 112 ¶6. The scope of the invention is therefore defined by the following claims.

The invention claimed is:

1. A negative pressure wound therapy system, comprising:
 a non-woven material configured to be positioned on an appendage, the non-woven material configured to communicate negative pressure to a wound on an appendage;
 a gas impermeable flexible housing material configured to be positioned over the non-woven material, the flexible housing material comprising a fold, the fold generally perpendicular to a longitudinal axis of the appendage, and
 wherein the flexible housing material comprises a gasket comprising a first portion and a second portion, the gasket configured such that when the flexible housing material is folded back upon itself to surround the wound on the appendage, the first portion of the gasket is adhered to the second portion of the gasket.

2. The negative pressure wound therapy system of claim 1, wherein the gasket is configured to form a seal around the circumference of the appendage, the seal configured to prevent the passage of gas.

3. The negative pressure wound therapy system of claim 1, wherein the flexible housing material further comprises a coating of adhesive on a skin-facing side of the flexible housing material.

4. The negative pressure wound therapy system of claim 1, wherein the gasket comprises a hydrogel.

5. The negative pressure wound therapy system of claim 1, wherein the flexible housing material comprises a liner.

6. The negative pressure wound therapy system of claim 1, wherein the gas impermeable housing material comprises an opening, the opening configured to allow the passage of negative pressure.

7. The negative pressure wound therapy system of claim 6, further comprising a port positioned over the opening.

8. The negative pressure wound therapy system of claim 7, further comprising a source of negative pressure connected to the port.

9. The negative pressure wound therapy system of claim 8, wherein the opening is located over the non-woven material.

10. The negative pressure wound system of claim 7, wherein the port is configured to be positioned over a top of the appendage.

* * * * *